US00PP24001P3

(12) United States Plant Patent
Fransen

(10) Patent No.: US PP24,001 P3
(45) Date of Patent: Oct. 22, 2013

(54) ***HOSTA* PLANT NAMED 'FORBIDDEN FRUIT'**

(50) Latin Name: ***Hosta* hybrid**
Varietal Denomination: Forbidden Fruit

(75) Inventor: Marco Fransen, Tel Aar (NL)

(73) Assignee: Vernooij V.O.F. (NL)

( * ) Notice: Subject to any disclaimer, the term of this patent is extended or adjusted under 35 U.S.C. 154(b) by 93 days.

(21) Appl. No.: 13/135,870

(22) Filed: Jul. 14, 2011

(65) Prior Publication Data

US 2013/0019364 P1 Jan. 17, 2013

(51) Int. Cl.
*A01H 5/00* (2006.01)

(52) U.S. Cl.
USPC ..... Plt./353

(58) Field of Classification Search
USPC ..... Plt./353
See application file for complete search history.

*Primary Examiner* — June Hwu
(74) *Attorney, Agent, or Firm* — Cassandra Bright

(57) ABSTRACT

A new and distinct *Hosta* cultivar named 'Forbidden Fruit' is disclosed, characterized by distinctive large, bright foliage with a green margin, vigorous plant habit and strong foliage, with good resistance to environmental stressors and large flowers. The new variety is a *Hosta*, typically used for outdoor ornamental purposes.

1 Drawing Sheet

Latin name of the genus and species: *Hosta* hybrid.
Variety denomination: 'FORBIDDEN FRUIT'.

BACKGROUND OF THE INVENTION

The new cultivar was discovered as an induced mutation using the known chemical colchicine, of *Hosta* hybrid 'Orange Marmalade' U.S. Plant Pat. No. 16,742 'Forbidden Fruit' was discovered by the inventor, Marco Fransen, a citizen of the Netherlands in October of 2008, at a research facility in Ter Aar, The Netherlands. The intent of the breeding program was to create new tetraploid *Hosta* hybrids with strong foliage and forming vigorous plants.

Directly after discovery of the tetraploid mutation, the inventor initiated cultivation in tissue culture, during October of 2008, in a commercial laboratory in Iribov Heerhugowaard, the Netherlands. Subsequently 'Forbidden Fruit' has been reproduced by micro-propagation in a commercial laboratory in Iribov Heerhugowaard, the Netherlands and has shown that the unique features of this cultivar are stable and reproduced true to type through several generations.

SUMMARY OF THE INVENTION

The cultivar 'Forbidden Fruit' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Forbidden Fruit' These characteristics in combination distinguish 'Forbidden Fruit' as a new and distinct *Hosta* cultivar:

1. Distinctive, bright foliage with a broad green margin.
2. Thick foliage resistant to environmental stressors.
3. Large foliage.

4. Vigorous plant.
5. Large flowers.

COMPARISON TO PARENT

Plants of the new cultivar 'Forbidden Fruit' are similar to plants of the parent; *Hosta* hybrid 'Orange Marmalade' in most horticultural characteristics, however, plants of the new cultivar 'Forbidden Fruit' are more vigorous and produce thicker, stronger leaves and thicker petioles than the parent variety. Additionally, the new variety produces larger foliage than 'Orange Marmalade'. Leaves of 'Forbidden Fruit' have a wider green margin than 'Orange Marmalade'.

COMMERCIAL COMPARISON

Plants of the new cultivar 'Forbidden Fruit' are comparable to the unpatented commercial variety *Hosta* hybrid Remember Me. The two *Hosta* varieties are similar in most horticultural characteristics; however, the new variety 'Forbidden Fruit' differs in producing larger flowers than those of comparator 'Remember Me'. Additionally, 'Forbidden Fruit' produces a stronger plant than comparator, 'Remember Me'.

Plants of the new cultivar 'Forbidden Fruit' are comparable to the unpatented commercial variety *Hosta* hybrid 'Captain Kirk'. The two *Hosta* varieties are similar in most horticultural characteristics; however, the new variety 'Forbidden Fruit' differs in producing larger flowers than those of comparator 'Captain Kirk'. Additionally, 'Forbidden Fruit' produces a stronger plant than the comparator, 'Captain Kirk'.

BRIEF DESCRIPTION OF THE PHOTOGRAPH

The accompanying photograph in FIG. 1 illustrates in full color a typical plant of 'Forbidden Fruit' grown outdoors. This plant is approximately 6 months old, shown in a 1 liter pot.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007 except where general terms of ordinary dictionary significance are used. The following observations and measurements describe 'Forbidden Fruit' plants grown in a commercial nursery in the Netherlands, from February of 2011 through June of 2011. Temperatures were 5° C. to 20° C. at night and 10° C. to 30° C. during the day. Measurements and numerical values represent averages of typical plant types. No growth regulators or special treatments were used.

Botanical classification: *Hosta* hybrid 'Forbidden Fruit'.

PROPAGATION

Time to initiate roots: Approximately 14 to 21 days at 23° C.

Root description: Fleshy with moderate side roots.

PLANT

Growth habit: Outwardly arching herbaceous perennial plant.

Height: Approximately 35 cm in a 1 liter pot.

Plant spread: Approximately 45 cm.

Growth rate: Moderate.

Branching characteristics: Branches emerge directly from the roots.

Age of plant described: Approximately 4 months from a stage 3 tissue culture.

FOLIAGE

Leaf:

- *Quantity per plant.*—Average 20.
- *Leaf type.*—Simple, basal emerging.
- *Average leaf length.*—Approximately 35 cm.
- *Average leaf width.*—Approximately 18 cm, at widest point.
- *Apex.*—Acute.
- *Base.*—Cordate.
- *Overall leaf shape.*—Obovate.
- *Overall leaf aspect.*—Arching.
- *Margin.*—Slightly undulating.
- *Texture of top surface.*—Smooth.
- *Texture of bottom surface.*—Smooth.
- *Appearance of top surface.*—Slightly leathery.
- *Appearance of bottom surface.*—Slightly leathery.
- *Pubescence.*—No pubescence on leaves.
- *Color.*—Young foliage upper side: Near RHS Yellow-Green 150B, center Green-Yellow 1C margin near RHS Green 137A. Young foliage under side: Near RHS Green-Yellow 1B, margin near RHS Green 137B. Mature foliage upper side: Near RHS Yellow 4B, center Green-Yellow 1D margin near RHS Green 137A. Mature foliage under side: Near RHS Yellow 4B, center Green-Yellow 1D margin near RHS Green 137A.
- *Venation.*—Type: Pinnate. Venation coloration upper side: Indistinguishable from foliage color. Venation coloration under side: Indistinguishable from foliage color.

Leaf petiole:

- *Length.*—Approximately 12 cm.
- *Width.*—Approximately 2.1 cm at widest point.
- *Texture.*—Glabrous, upper and lower surfaces.
- *Color.*—Upper side: Near RHS Green-Yellow 1B. Under side: Near RHS Yellow-Green N144C.
- *Strength.*—Very strong.

Other foliage characteristics: Thick foliage, resistant to mechanical damage and environmental stressors.

FLOWER

Natural flowering season: Late Spring into Summer.

Inflorescence type and habit: Single, campanulate arranged in racemes.

Rate of flower opening: Lowest flower opens first, all flowers have opened in approx. 2 weeks.

Flower longevity on plant: Approx. 2 weeks.

Quantity of flowers: Average: 13 flowers per raceme.

Raceme size:

- *Height.*—Approximately 14.9 cm, from lowest flower to top of Inflorescence.
- *Width.*—Approximately 9.6 cm.

Flower:

- *Perianth.*—Arrangement: Campanulate.
- *Overall flower size.*—Length: Approximately 6.0 cm. Width: Approximately 3.9 cm at widest point.

Color:

- *Tepals.*—When opening: Outer surface: White; Near RHS NN155D, base tinged purple; near RHS 76B, top tinged lighter; near RHS 76C. Inner surface: White; Near RHS NN155D, base and top tinged purple; near RHS 76C.
- *Fully opened.*—Outer surface: White; Near RHS NN155D but whiter, top very slightly tinged purple; near RHS 76D. Inner surface: White; Near RHS NN155D but whiter, base slightly tinged purple; near RHS 76C. Color Changes when Aging: Near RHS NN155D.

Sepals or bracts:

- *Quantity.*—One bract is placed under each individual flower.
- *Shape.*—Ovate, concave.
- *Length.*—Approximately 2.6 cm.
- *Diameter.*—Approximately 0.8 cm.
- *Color.*—Outer surface: Yellow-green; Near RHS 147C. Inner surface: Yellow-green; Near RHS N146D. Color Changes when Aging: Yellow-green; Near RHS 145B.

Bud:

- *Shape.*—Obovate.
- *Length.*—Approximately 2.6 cm.
- *Diameter.*—Approximately 1.0 cm.
- *Color.*—Purple; Near RHS 76C, base darker; Near RHS 76A to 76B.

Pedicels:

- *Length.*—Approximately 0.6 cm.
- *Width.*—Approximately 0.2 cm.
- *Aspect.*—Placed to the petiole in an average angle of 30° (0°=horizontal), curved downward in an average angle of −30° (0°=horizontal).
- *Color.*—Yellow-green; Near RHS 147C, tinged greyed green; Near RHS 197A.

Scape:

*Length.*—Approximately 58.5 cm.

*Width.*—Approximately 0.4 cm.

*Angle.*—Near vertical.

*Strength.*—Strong.

*Color.*—Yellow-green; Near RHS 150 B to 151C.

Fragrance: No.

REPRODUCTIVE ORGANS

Stamens:

*Number.*—Average 6.

*Filament length.*—Approximately 5.7 cm.

*Filament color.*—White; Near RHS NN155D.

*Anther length.*—Approximately 0.5 cm.

*Anther color.*—Near RHS 176B.

*Anther shape.*—Oblong, dorsifixed.

*Pollen.*—Moderate, coloured Yellow-Orange; near RHS 15A.

Pistil:

*Number.*—1.

*Length.*—Approximately 5.5 cm.

*Style color.*—White; Near RHS NN155D, yellow-green towards the base; Near RHS 145C to 145D.

*Stigma.*—Shape: Club-shaped. Color: White; Near RHS N155D.

*Ovary color.*—Yellow-green; Near RHS 145B.

Fruits: Have not been observed to date.

OTHER CHARACTERISTICS

Disease resistance: Better resistance to diseases or pests has been observed in this variety, due to the strong, thick foliage.

Temperature tolerance: Hardy perennial, tolerates a temperature range from approximately −30° C. to at least 40° C.

Drought tolerance: No tolerance for drought.

What is claimed is:

1. A new and distinct cultivar of *Hosta* plant named 'Forbidden Fruit' as herein illustrated and described.

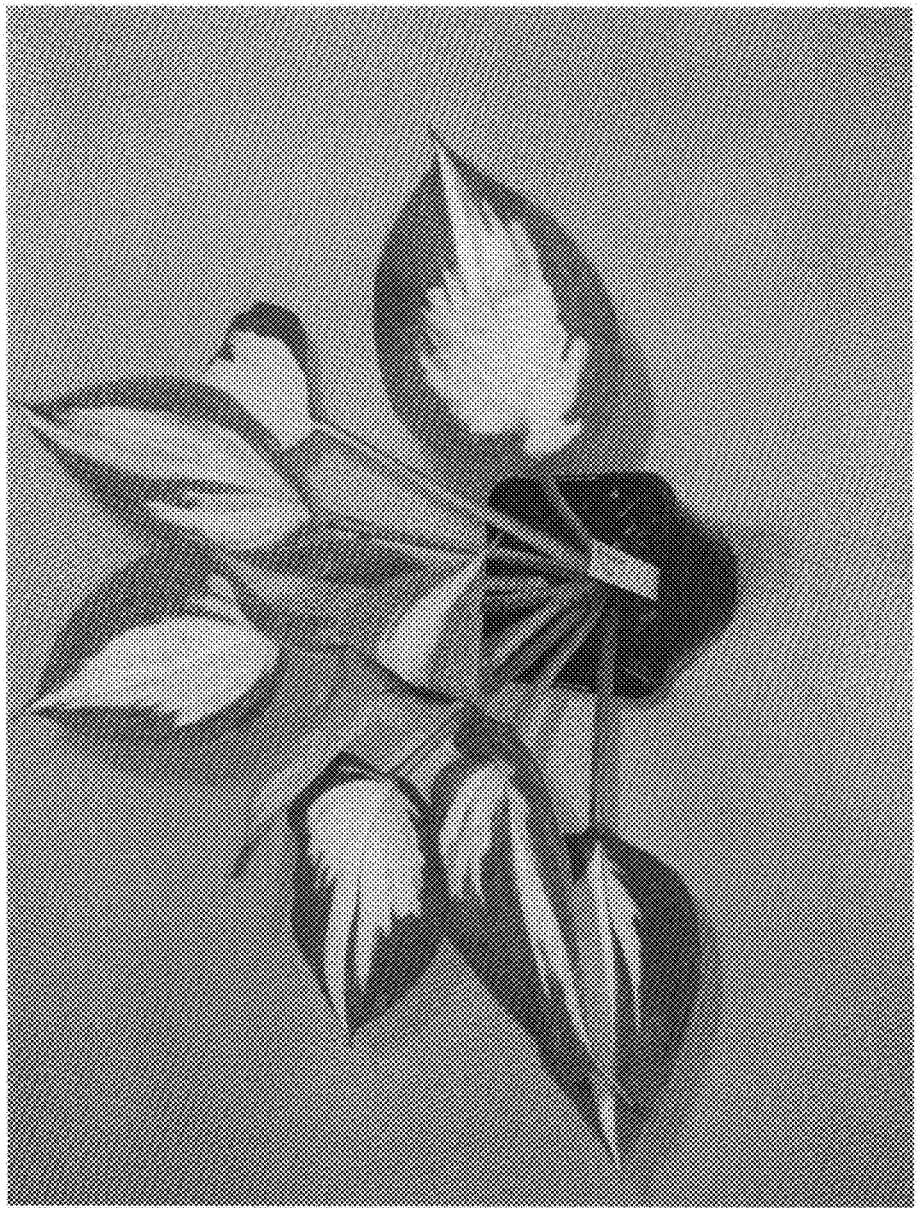

* * * * *